United States Patent [19]
Villani

[11] Patent Number: 5,875,019
[45] Date of Patent: Feb. 23, 1999

[54] SYSTEM FOR THE DETERMINATION, THE EVALUATION AND THE CONTROL OF THE REFRACTIVE AND ACCOMMODATIVE STATUS OF THE EYE

[76] Inventor: Gherardo Villani, via IV Novembre, 20, 06049 Spoleto, Italy

[21] Appl. No.: 849,992

[22] PCT Filed: Nov. 21, 1995

[86] PCT No.: PCT/IT95/00196

§ 371 Date: Jun. 13, 1997

§ 102(e) Date: Jun. 13, 1997

[87] PCT Pub. No.: WO97/18747

PCT Pub. Date: May 29, 1997

[51] Int. Cl.⁶ ........................................................ A61B 3/10
[52] U.S. Cl. ............................ 351/211; 351/215; 351/221
[58] Field of Search ...................................... 351/211, 205, 351/215, 214, 221; 600/558

[56] References Cited

U.S. PATENT DOCUMENTS 3,880,501  4/1975  Munnerlyn ............................... 351/215
5,258,791  11/1993  Penney et al. ........................... 351/211
5,787,890  8/1998  Reiter et al. ............................. 351/215

FOREIGN PATENT DOCUMENTS 563454  10/1993  European Pat. Off. .

*Primary Examiner*—Huy Mai
*Attorney, Agent, or Firm*—Beveridge, DeGrandi, Weilacher & Young, L.L.P.

[57]  ABSTRACT

The system for the determination, the evaluation and the control of the refractive and accommodative status of the eye according to the present invention includes:

a scanner (AN) to be placed before the eye optically corrected or not, and completely or partially consisting of material polarizing the optical radiation, and divided into two parts with perpendicular polarization and;

an illuminated target (MR), completely or partially consisting of parts out of polarizing material, having the polarizing axis parallel or perpendicular to each other, whereby said target may comprise means for moving said parts and for rotating said target onto the longitudinal axis.

14 Claims, 2 Drawing Sheets

SYSTEM FOR THE DETERMINATION, THE EVALUATION AND THE CONTROL OF THE REFRACTIVE AND ACCOMMODATIVE STATUS OF THE EYE

The present invention concerns a system for the determination, the evaluation and the voluntary control of the refractive and accommodative status of the eye. The system includes a scanner, completely or partially consisting of material having the capacity of polarizing the optical radiations, and a target consisting completely or partially of material having the same polarizing capacities. The uneasiness sometimes linked to the accommodation, i.e. to the power increase of the optic eye system, mainly due to the shape variation of the crystalline lens, is well known, as well as the need of evaluating the exerted accommodation and its entity.

Also the need of evaluating the kind and the entity of the refractive error or ametropia is known, i.e. the surplus or lack of power of the eye, such as not to allow—in conditions of not exerted accommodation—the correct focusing on the retina of the image of a target placed at the optical infinity.

A power surplus determines the formation of the image before the retina (myopia), a lack of power determines the formation of the image beyond the retina (hypermetropia), a difference of power between the two meridians of the optic system causes the formation of two images in the shape of segments perpendicular to each other (astigmatism).

The main aim of the present invention is allowing the evaluation of the kind and entity of refractive error of the eye, the measuring of the exerted accommodation, the voluntary control of the accommodation and of the reduction or the solution of psychophysical uneasiness and the consequences thereof connected to accommodation.

The aim set forth is reached by means of the system for the determination and control of the refractive and accommodative status of the eye according to the present invention, consisting of:

a scanner, through which a target is examined, with the eye optically corrected or not, and completely or partially consisting of material polarizing the optical radiation, and divided into two parts with polarization axis perpendicular or nearly perpendicular to each other. The visual axis of the eye to be examined passes near the separation line between the two polarized half-fields or through the same;

a target, completely or partially consisting of parts out of material polarizing the optical radiation, having the polarizing axis parallel or nearly parallel, perpendicular or nearly perpendicular to each other, possibly including means for moving the parts and possibly means for rotating all or a part of the target onto the longitudinal axis, so that as the scanner and the target lie on front-parallel planes or on nearly front-parallel planes, and as the scanner is placed, with respect to the target, in such a way that the polarizing axis of the polarized parts of the target is as parallel and/or perpendicular as possible to the polarization axis of each of the polarized parts of the scanner, only the optical radiation, coming from the non-polarized parts and from the parts of the target polarized parallel to the polarization axis of the part of the scanner, passes from one of the polarized parts of the scanner; while the optical radiation coming from those parts of the target polarized perpendicularly to the axis, does not pass or passes in a negligible quantity. Furthermore, the target may be projected onto appropriated screens, like virtual or real screen(s), by means of appropriate means.

For what concerns the image seen through the scanner, there are two alternatives in which the polarized parts of the target are seen by contrast with the background:

the polarized parts of the target are on a low luminance background, so that the background and the polarized part(s) of the target with polarization axis perpendicular to one of the polarized parts of the scanner, seen from the part of the scanner, have a similar luminance, such as to be not, or nearly not, distinguished due to lack or shortage of contrast between target and background, while the part(s) of the target with the polarization axis parallel to that of the part of the scanner are seen, through the part, light, i.e. bright, on a dark background, and may be distinguished from same. A similar process is deserved for the other part of the scanner;

the polarized parts of the target are on a background with an appropriate luminance, sufficient for that the background and the polarized part(s) of the target, with polarization axis parallel to the one of one of the polarized parts of the scanner, seen from the part of the scanner, have such a similar luminance that they can nearly not be distinguished or can not be distinguished for lack or shortage of contrast between target and background, while the part(s) of the target with the polarization axis perpendicular to that of the part of the scanner are seen, through the part, dark on a light background, i.e. bright and distinguishable from the same. A similar process is deserved to the other part of the scanner.

The advantages according to the present invention are, beyond those due to the provided use:

a reduction of the myopia progression due to accommodation and to the accommodative system;
  diagnostic action for anomalies of the accommodation and of the accommodation system;
  a therapeutic-rehabilitating action for the functional anomalies of the accommodation and of the accommodative system;
  reduction of the entity of the tonic accommodation;
  the distancing of the remote accommodation point;
  to initiate new studies linked to accommodation and to the accommodative system;
  measuring of the accommodative power;
  to be used in vision training procedure(s);
  evaluation and measuring of the (possible) difference between exerted accommodation and accommodative stimulus;
  improvement of the efficiency of accommodation and of the accommodative system;
  evaluation and measuring of the exerted accommodation;
  the pointing out of latent hypermetropia, or of part of it;
  the activation of psychi-physiological process(es) related to accommodation and to the accommodation system.

The present invention will be described more in detail hereinbelow relating to the enclosed drawings in which some embodiments are shown.

The enclosed figures show one of the possible systems, according to the present invention, for the determination, the evaluation and the control of the refractive and accommodative status of the eye, in which the optical radiation coming from the part a of the target MR—polarized in parallel—passes through the part A of the scanner AN, and not through the part B of the same, as it is polarized in perpendicular with respect to the polarization axis of the same, and forms an image a'; in a similar way the part b of the target forms an image b'.

When the power of the optic eye system varies, be the eye corrected or not, and also the distance between the secondary principal plane P' and the retina R, the image of the target may be:

- before the retina R (in this case, the parts a' and b' of the image of the target on the retina appear moved to each other);
- onto the retina R (in this case, the parts a' and b' of the image of the target onto the retina appear not moved to each other);
- beyond the retina R (in this case, the parts a' and b' of the image of the target onto the retina appear moved to each other, and in a sense opposite to that described above).

The position of the image on the retina varies according to many factors, between which the most important are:

- the distance between target and primary principal plane of the optic eye system, corrected or not;
- ametropia of the eye;
- eventual exerted accommodation;
- eventual optic correction;
- spectral composition of the luminance source(s);
- possible aberrations, anisotropies, nonhomogeneities of the optical media and of the eye.

The entity of the moving of the parts a' and b' of the image onto the retina of the parts a and b of the target MR, occurs according to the distance from the retina at which the image of the target is formed, given by the optic eye system.

Figure 2:
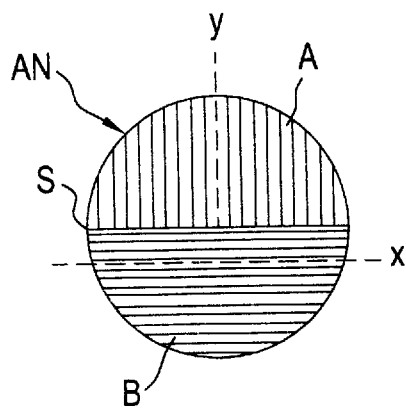
FIGS. 2, 3 and 3b show the details of a scanner and of a target, with possibility of moving same.
Figure 3A:
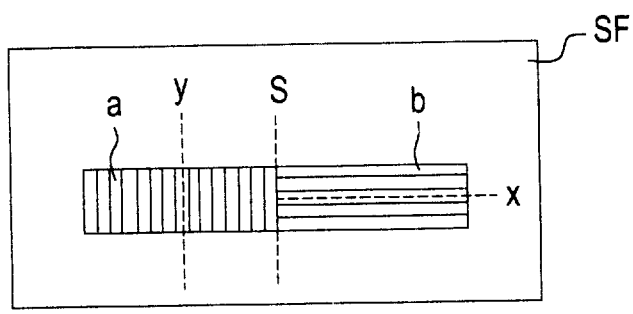

Relating in particular to FIGS. 2, 3, on the scanner AN and on the target MR are shown:

- a half-field A of polarizing material;
- an axis Y for the polarization of the half-field A;
- a half-field B of polarizing material;
- an axis X for the polarization of the half-field B;
- a line S for separating the half-field A and the half-field B;
- a part a of the target, of polarizing material;
- an axis Y for polarizing a;
- a part b of the target, of polarizing material;
- an axis X for polarizing b;
- a line S' for separating a and b.

Figure 3B:
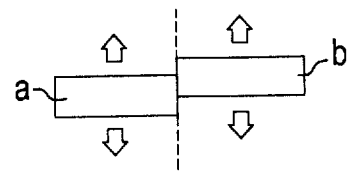

It is possible to physically move a with respect to b (or b with respect to a) along a separation line, e.g. on an axis parallel to axis Y, as shown in FIG. 3B.

Figure 4:
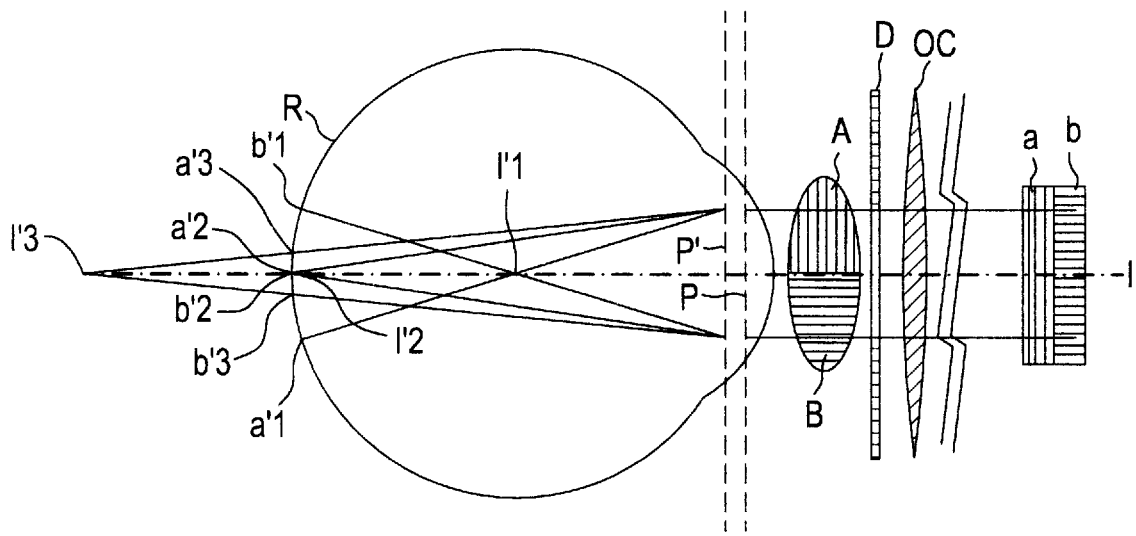
FIG. 4 shows the formation of the images with the system according to the present invention.

Furthermore, in FIG. 4 the following details are shown:

I=meeting point between visual axis and target
P=primary principal plane
P'=secondary principal plane
$a_1'$ and $b_1'$=images on the retina of a and b when $I_1'$ (image of the target given by the optic eye system) is before the retina ($I_1'$P' RP')
$a_2'$ and $b_2'$=images on the retina of a and b when $I_2'$ (image of the target given by the optic eye system) is on the retina ($I_2'$ P'=RP') $a_3'$ and $b_3'$=images on the retina of a and b when $I_3'$, (image of the target given by the optic eye system) is behind the retina ($I_3'$P' RP').

For what concerns the functioning of the system according to the present invention, if

- the distance between target and primary principal plane of the optic eye system, corrected or not;
- the possible optic correction;
- the spectral composition of the luminance source(s), and
- possible aberrations, anisotropies, nonhomogeneities of the optical media and of the eye are placed as fixed, and therefore as parameters, or are fixed, the refraction error of the eye and the possible exerted accommodation remain as variable elements, so that the refractive and/or accommodative status of the eye may be (subjectively) evaluated and the entity of the ametropia and/or of the exerted accommodation may be measured, e.g. evaluating and measuring the apparent moving of the parts a' and b', in the example physically moving the parts a and b of the target until the alignment of the parts a' and b' is reached (and thus restoring the shape of the target as if it was seen without the scanner); or placing before the eye a lens or lenses of such a power as to reach, as shown in the example, the alignment of parts a' and b'.

If accommodation is exerted, it is possible to control if it is exerted in surplus, in the right entity or in shortage with respect to the one requested for focusing at the distance at which the target is placed, furthermore allowing a retroactive voluntary control (by biofeedback) of the exerted accommodation, in the example evaluating the alignment or not of the parts a' and b' of the target (and the possible variations of the position between a' and b'—or between b' and a'—in time).

Figure 1:
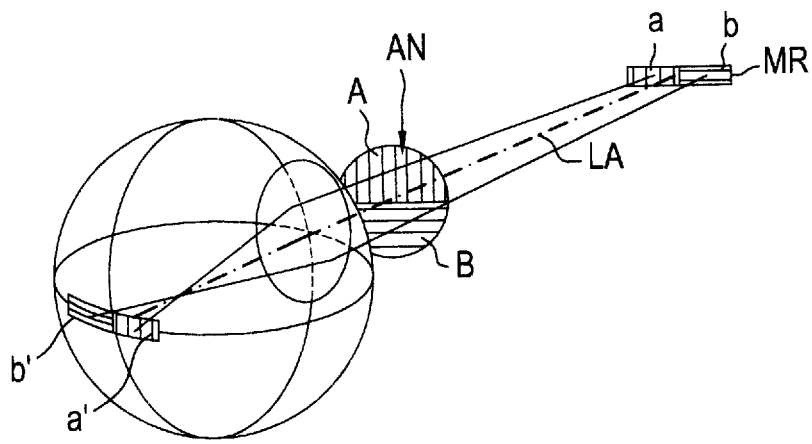
FIG. 1 shows a scheme of a system for the determination, the evaluation and the control of the refractive and accommodative, static and dynamic status of the eye, according to the present invention.
Figure 5:
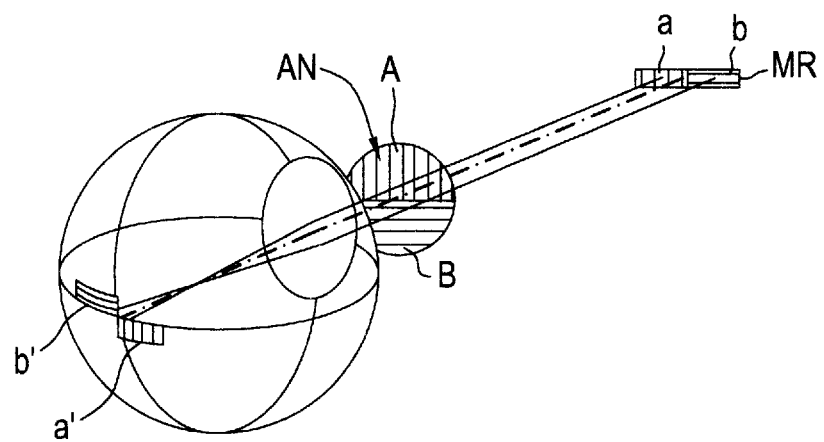
FIG. 5 shows an example of an image seen when the image of the target given by the system according to the present invention lies before the retina.

The system according to the present invention includes a scanner (analyzer) and a target as shown in FIGS. 1 and 5. The analyzer is divided in two semi-fields, perpendicularly polarized one to the other. The target is realized in such a way that from one polarized semi-field the polarized part of the target with polarization axis parallel to said part of the analyzer can be seen (in the case of target with lightened polarized parts onto an opaque, dark background), or with the polarization axis perpendicular to the one of the analyzer (and the perpendicularly polarized parts are seen dark on the lightened background).

The target and its polarized parts may have many shapes and dimensions; in the enclosed figures, a simple target is shown, consisting only of polarized elements a and b.

The target MR is seen through parts A and B of the analyzer AN, with the eye optically adjusted or not; the image given by the optical system is formed before the retina, on the retina or beyond the retina, mainly according to the distance of the target, to the refractivity device and to the relative location of a and b. If there is no adjustment and through the analyzer we look at the target, placed at the optical infinity, we will see $\alpha$ and $\beta$, which represent the projection into the space of the retinal images a' and b' respectively of the polarized parts a and b of the target; and these may appear;

- aligned: in this case, the subject is emmetropic;
- non aligned: in this case, the subject is ametropic.

The existence of nonalignment, which may be easily measured by means of the Vernier sharpness, is a direct function of the ametropy entity, i.e., the greater the nonalignment, the greater the ametropy; the relative position of $\alpha$ and $\beta$ will be dependent on the polarization axis of the parts, on the polarization axis of the analyzer and on the kind of target, but however it will be in an opposite way in case of myopy with respect of the case of hypermetropia (in the example shown in the figure, relating to a case of hypermetropia, part α appears to be higher than part β6; the contrary occurs in case of myopy); conventionally, the displacement due to myopy is shown with a plus +, the one caused by hypermetropia with a minus −. The measuring and the optical compensation of ametropy may be performed as follows:

- by placing before the eyes positive or negative lens such as to align α and β;
- moving a with respect to b until the alignment with a and α is obtained, and measuring the entity of the adjustment (from the relation that links the apparent angular movement between α and β and ametropy). If an adjustment is performed, then the size of the adjustment will be added to ametropy. Therefore, the present system has the function of a subjective refactometer, and may be used for determining the refractive and the adjustment for any distance. Among the many possible applications of the present system, the most interesting concern:
- measuring of ametropy (in case of astigmatism, target and analyzer are rotated);
- balancing of the binocular vision (also in case of unilateral relative amblyopia);
- control of amending;
- determining latent hypermetropia;
- reduction of the amending component and of the subjective adjusting in myopies;
- valuation and control of the amending lag;
- diagnosis and therapy of the amending anomalies;
- valuation of the response of the visual system to the adjusting lens.

In possible variants of the system according to the present invention, the scanner according to above specification may be provided with a diaphragm D or not, may be rotated on the longitudinal axis LA (rotation means not shown) and may be linked or not to optical compensation OC and may be part of other equipment.

In further variants, said target may have other structural elements (e.g. letters from the alphabet, gratings, etc;) so as to allow the control of the focusing of the target, which in turn may be rotated (on the longitudinal axis).

I claim:

1. An optical system for use in evaluating an eye comprising:
   - an illuminated target centered on and substantially perpendicular to a longitudinal axis extending from the eye to be examined, said illuminated target including
     - a first polarized part with a substantially vertical polarizing axis, and
     - a second polarized part with a substantially horizontal polarizing axis, said second polarized part is adjacent to said first polarized part such that said first polarized part and said second polarized part slide relative to each other, and
   - a scanner spaced from said illuminated target along the longitudinal axis, said scanner is substantially perpendicular to and divided about the longitudinal axis into
     - a first half-field of polarizing material with a substantially vertical polarizing axis, and
     - a second half-field of polarizing material with a substantially horizontal polarizing axis; and wherein
   - said illuminated target projects through said scanner onto the eye where parts of said illuminated target have a polarizing axis in alignment with half-fields of said scanner.

2. The optical system according to claim 1, further comprising a screen on which said illuminated target is mounted, said screen is negligibly illuminated such that a part of said illuminated target having a polarizing axis perpendicular to a half-field of said scanner matches the luminance of said screen on the eye.

3. The optical system according to claim 1, further comprising a screen on which said illuminated target is mounted, said screen is illuminated such that a part of said illuminated target having a polarizing axis parallel to a half-field of said scanner matches the luminance of said screen on the eye.

4. The optical system according to claim 1, further comprising a diaphragm centered about the longitudinal axis and spaced between said screen and said illuminated target.

5. The optical system according to claim 1, further comprising a rotation means to simultaneously rotate said illuminated target and said scanner together about the longitudinal axis.

6. The optical system according to claim 1, further comprising an optic compensator centered about the longitudinal axis and spaced between said scanner and said illuminated target.

7. The optical system according to claim 1, wherein said illuminated target further includes means for controlling the focusing of the eye.

8. An optical system for use in evaluating an eye comprising:
   - a screen centered on and substantially perpendicular to a longitudinal axis extending from the eye to be examined,
   - an illuminated target spaced from said screen at an angle such that said illuminated target projects on to said screen, said illuminated target including
     - a first polarized part with a substantially vertical polarizing axis, and
     - a second polarized part with a substantially horizontal polarizing axis, said second polarized part is adjacent to said first polarized part such that said first polarized part and said second polarized part slide relative to each other, and
   - a scanner spaced from said illuminated target along the longitudinal axis, said scanner is substantially perpendicular to and divided about the longitudinal axis into
     - a first half-field of polarizing material with a substantially vertical polarizing axis, and
     - a second half-field of polarizing material with a substantially horizontal polarizing axis; and wherein
   - said illuminated target projects through said scanner onto the eye where parts of said illuminated target have a polarizing axis in alignment with half-fields of said scanner.

9. The optical system according to claim 8, wherein said screen is negligibly illuminated such that a part of said illuminated target having a polarizing axis perpendicular to a half-field of said scanner matches the luminance of said screen on the eye.

10. The optical system according to claim 8, wherein said screen is illuminated such that a part of said illuminated target having a polarizing axis parallel to a half-field of said scanner matches the luminance of said screen on the eye.

11. The optical system according to claim 8, further comprising a diaphragm centered about the longitudinal axis and spaced between said screen and said illuminated target.

12. The optical system according to claim 8, further comprising a rotation means to simultaneously rotate said scanner about the longitudinal axis and said illuminated target such that the projected image on said screen rotates in conjunction with the rotation of said scanner.

13. The optical system according to claim 8, further comprising an optic compensator centered about the longitudinal axis and spaced between said screen and said scanner.

14. The optical system according to claim 8, wherein said illuminated target further includes means for controlling the focusing of the eye.

* * * * *